(12) United States Patent
Wieters

(10) Patent No.: US 10,285,572 B2
(45) Date of Patent: May 14, 2019

(54) ACTUATOR FOR A SURGICAL INSTRUMENT

(71) Applicant: OLYMPUS WINTER & IBE GMBH, Hamburg (DE)

(72) Inventor: Martin Wieters, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 870 days.

(21) Appl. No.: 14/694,488

(22) Filed: Apr. 23, 2015

(65) Prior Publication Data

US 2015/0223674 A1 Aug. 13, 2015

Related U.S. Application Data

(63) Continuation of application No. PCT/EP2013/003006, filed on Oct. 7, 2013.

(30) Foreign Application Priority Data

Oct. 23, 2012 (DE) .......................... 10 2012 219 354

(51) Int. Cl.
*A61B 1/00* (2006.01)
*G02B 23/24* (2006.01)

(52) U.S. Cl.
CPC ........ *A61B 1/00188* (2013.01); *A61B 1/0011* (2013.01); *A61B 1/00057* (2013.01);
(Continued)

(58) Field of Classification Search
CPC ............ A61B 1/00128; A61B 1/00137; A61B 1/00158; A61B 1/00188; A61B 1/00057;
(Continued)

(56) References Cited

U.S. PATENT DOCUMENTS 4,952,041 A * 8/1990 Sandall .................... G02B 7/10
359/422
5,540,650 A * 7/1996 Smith .................... A61B 1/002
356/241.5
(Continued)

FOREIGN PATENT DOCUMENTS

CN 101511256 A 8/2009
CN 102292569 A 12/2011
(Continued)

OTHER PUBLICATIONS

International Search Report dated Jan. 17, 2014 issued in PCT/EP2013/003006.
(Continued)

*Primary Examiner* — David M Fenstermacher
*Assistant Examiner* — Bobby Rushing, Jr.
(74) *Attorney, Agent, or Firm* — Scully, Scott, Murphy & Presser, P.C.

(57) ABSTRACT

An actuator for a surgical instrument. The actuator including: a sliding tube; and a rotor arranged in said sliding tube; wherein the sliding tube has at one end a receiving cavity for a rotor positioning key, the receiving cavity being configured such that after the rotor positioning key has been positioned in the receiving cavity, and after the rotor positioning key has been twisted in the receiving cavity, the rotor positioning key is releasably locked.

15 Claims, 2 Drawing Sheets

(52) U.S. Cl.
CPC ...... *A61B 1/00096* (2013.01); *A61B 1/00158*
(2013.01); *G02B 23/2476* (2013.01); ***Y10T
74/18568*** (2015.01)

(58) Field of Classification Search
CPC .............. A61B 1/00096; A61B 1/0011; G02B
23/2476; G02B 7/10; G02B 23/24
USPC ....... 600/128, 106, 127, 129, 137, 139, 163,
600/162; 411/549, 550; 403/3, 4, 348,
403/353, 359.3, DIG. 1; 74/829
See application file for complete search history.

(56) References Cited

U.S. PATENT DOCUMENTS

| | | | | |
|---|---|---|---|---|
| 6,155,973 | A * | 12/2000 | Howes | G02B 23/2484 |
| | | | | 359/683 |
| 6,254,303 | B1 * | 7/2001 | Falat | B23B 31/113 |
| | | | | 403/321 |
| 6,402,701 | B1 * | 6/2002 | Kaplan | A61B 10/0233 |
| | | | | 600/567 |
| 6,409,658 | B1 | 6/2002 | Mitsumori | |
| 6,764,439 | B2 * | 7/2004 | Schaaf | A61F 9/00781 |
| | | | | 600/104 |
| 6,971,847 | B2 * | 12/2005 | Tiemann | F01D 9/042 |
| | | | | 403/230 |
| 7,226,459 | B2 * | 6/2007 | Cesarini | A61B 17/32002 |
| | | | | 600/566 |
| 7,449,004 | B2 * | 11/2008 | Yamada | A61B 17/2202 |
| | | | | 600/104 |
| 7,950,562 | B2 * | 5/2011 | Beardsley | A61B 17/07207 |
| | | | | 227/175.1 |
| 8,858,111 | B2 * | 10/2014 | Donohue | B25G 1/04 |
| | | | | 403/348 |
| 9,205,190 | B2 * | 12/2015 | Remde | A61M 5/1413 |
| 2002/0123664 | A1 * | 9/2002 | Mitsumori | A61B 1/00096 |
| | | | | 600/130 |
| 2009/0156898 | A1 | 6/2009 | Ichimura | |
| 2012/0011951 | A1 | 1/2012 | Gaecther | |
| 2013/0147583 | A1 * | 6/2013 | Schiepp | F01L 1/46 |
| | | | | 335/229 |
| 2013/0190552 | A1 * | 7/2013 | Leblans | H04R 25/606 |
| | | | | 600/25 |
| 2013/0193778 | A1 | 8/2013 | Wieters et al. | |
| 2016/0070070 | A1 * | 3/2016 | Bhagavatula | A61B 5/0066 |
| | | | | 385/26 |
| 2017/0097512 | A1 * | 4/2017 | Haymond | G02B 27/2257 |

FOREIGN PATENT DOCUMENTS

| | | | | |
|---|---|---|---|---|
| DE | | 1253407 B | 11/1963 | |
| DE | | 2423722 A | 5/1974 | |
| DE | | 2423722 | 12/1974 | |
| DE | | 19618355 A1 | 11/1997 | |
| DE | | 102011006814 A1 | 1/2012 | |
| DE | | 102014208652 A1 * | 11/2015 | ......... A61B 1/00096 |
| EP | | 2057930 A1 | 5/2009 | |
| JP | | 2008-054843 A | 3/2008 | |
| JP | | 2009-071967 A | 4/2009 | |
| WO | WO 2007/129987 A1 | | 11/2007 | |
| WO | | 2012/003897 A1 | 1/2012 | |
| WO | WO-2013007356 A1 * | | 1/2013 | ......... A61B 1/00096 |

OTHER PUBLICATIONS

Chinese Office Action and Search Report dated Mar. 18, 2016 issued in Application No. or Patent No. 201380055193.4.

* cited by examiner

ACTUATOR FOR A SURGICAL INSTRUMENT

CROSS-REFERENCE TO RELATED APPLICATION

The present application is a continuation of PCT/EP2013/003006 filed on Oct. 7, 2013, which is based upon and claims the benefit of DE 10 2012 219 354.5 filed on Oct. 23, 2012, the entire contents of each of which are incorporated herein by reference.

BACKGROUND

Field

The present application relates to an actuator, particularly a bistable actuator, for a surgical instrument, particularly an endoscope, with a sliding tube to accommodate a rotor and a rotor arranged in said sliding tube. Furthermore, the present application relates to a rotor positioning key for a rotor of a, particularly bistable, actuator.

Prior Art

An endoscope with a distally arranged objective is known from DE 196 18 355 C2, the image of which is forwarded to the proximal end by an image forwarder and that has at least one optical element like a lens group, which is shiftable in the direction of the optical axis for focussing and/or for changing the focal length by a microdrive, wherein the microdrive has at least one rotationally symmetrical axially movable sleeve, which surrounds and receives the lenses or respectively the optical element of the movable lens group and wherein the sleeve is made of a permanently magnetic material and is movable in a magnetic field, which is generated by a spool arrangement. In order to move and to hold the sleeve, an electromagnetic field is generated continuously.

An endoscope with a distally radiating illumination device for a body cavity part to be observed and an image conductor is known from DE 1 253 407 B, which captures the illuminated image via an objective that is adjustable in the axial direction and directs it to an ocular or a camera, wherein the objective is adjustable for at least two image sharpness settings from one position into another position with respect to the distal end of an image conductor through electromagnetic manipulation of an objective mount serving as an anchor. At least one of the two positions is hereby evoked by a permanently present electromagnetic field and the other position by the effect of a spring.

Moreover, an electromagnetic actuator for a surgical or medical instrument, in particular an endoscope, is described in DE 10 2011 006 814 A1.

SUMMARY

An object is to improve the handling of an actuator for a surgical instrument in a simple manner.

This object is solved through an actuator, particularly a bistable actuator, for a surgical instrument, particularly an endoscope, with a sliding tube to accommodate a rotor and a rotor arranged in said sliding tube, which is further developed in that the sliding tube has at one end a receiving cavity for a rotor positioning key, wherein the receiving cavity is designed such that, after the rotor positioning key has been positioned in the receiving cavity and after the rotor positioning key has been twisted in the receiving cavity, the rotor positioning key is releasably locked.

When using a rotor positioning key, which is arrangeable in the receiving cavity of the sliding tube, the stroke of a rotor in the sliding tube of the actuator can be adjusted in a simple manner, since in the interaction between the receiving cavity and the rotor positioning key, the rotor positioning key is securely held on the end of the sliding tube, wherein the stroke of the rotor is determined by the thickness of the key head of the rotor positioning key. A fixed spacer element is hereby provided during the setting of the positioning travel of the rotor. After the receiving of the rotor positioning key in the receiving cavity, the rotor positioning key is twisted so that, after execution of the twist, the rotor positioning key is brought into a corresponding setting position for the rotor.

For this, the receiving cavity has a rotary gate, which in the interaction with the rotor positioning key, ensures a twisting of the rotor positioning key and a locking of the key. The rotary gate thus has a function of a rotary guide device for the rotor positioning key.

An actuator for a surgical or medical instrument, particularly an endoscope, is understood as a, preferably bistable, actuator. The electromagnetic actuator hereby has a stator and a displaceable rotor. The rotor is hereby located inside the sliding tube. In one embodiment, the rotor itself has at least one paramagnetic and/or ferromagnetic material, wherein the rotor is shiftable from a first position into a second position by supplying an electromagnetic field. The rotor is thereby held in a first position by a permanent magnetic field and, after being shifted into a second position, is held in the second position by a permanent magnetic field.

Additional details about an electromagnetic, bistable actuator of a surgical or medical instrument are described in DE 10 2011 006 814 A1, wherein the disclosed content of this document is incorporated herein by reference in its entirety.

Moreover, one embodiment of the actuator is characterized in that the receiving cavity has a stop for the rotor positioning key. A defined stop point for the rotor positioning key is hereby provided in the axial direction, i.e. the direction of movement of the rotor.

Moreover, the receiving cavity of the sliding tube is adjusted in a shape-complementary manner and/or functionally complementary manner to the contour of a key head of the rotor positioning key.

The receiving cavity thereby preferably has a non-round and/or star-shaped, in particular polygonal-like or polygonal, cross-sectional contour.

In the interaction of the rotary gate of the sliding tube and of the rotor positioning key, which is arranged and rotated in the receiving cavity of the sliding tube, and due to the shape- and functionally complementary design of the receiving cavity and of the key head of the rotor positioning key interacting with the receiving cavity, an end position of the rotor in the sliding tube is provided as a stop position in a simple manner. The rotor positioning key is hereby rotated around its axis in the rotary gate provided for this purpose after arrangement in the receiving cavity, whereby, due to the projecting shape of the key head, the key head of the rotor positioning key is locked at a defined distance between the stop in the sliding tube and the end face of the rotor positioning key for the setting of the stroke length of the rotor in the sliding tube.

After the insertion and the twisting of the rotor positioning key, the rotor in the sliding tube, if applicable together with a stopper or the like, is pressed in the sliding tube, with force against the stop surface of the locked key head, which faces the rotor. In this state, e.g. a stopper is then connected or respectively joined with the sliding tube e.g. through an adhesive process or the like. The rotor positioning key is subsequently rotated back in the receiving cavity in the rotary gate and removed from the receiving cavity so that space is created for the stroke of the rotor in the sliding tube.

Moreover, the object is solved by a rotor positioning key for a rotor of a, particularly bistable, actuator, of a surgical instrument, particularly an endoscope, wherein the rotor positioning key is releasably lockable in a sliding tube of the actuator and is twistable in a rotary gate, in particular the receiving cavity. In particular, the sliding tube of the actuator is designed as described above.

In a further development, the rotor positioning key preferably has an end-side, widened key head for arrangement and for insertion into the receiving cavity of the sliding tube or respectively into the rotary gate provided for the rotor positioning key, and a key shaft for twisting the rotor positioning key, preferably in the rotary gate.

A secure arranging and guiding of the key head in the receiving cavity is thereby achieved, wherein the key head interacts with the receiving cavity of the sliding tube upon arrangement of the key head. The key head of the rotor positioning key is preferably designed in a non-round and/or star-shaped, particularly polygonal-like, manner.

Moreover, the object is solved through use of a rotor positioning key described above for an actuator of a surgical instrument, in particular in combination with an actuator described above. For this, we refer expressly to the above explanations.

Further characteristics will become apparent from the description of embodiments according to the invention together with the claims and the included drawings. Embodiments a can fulfil individual characteristics or a combination of several characteristics.

BRIEF DESCRIPTION OF THE DRAWINGS

The invention is described below, without restricting the general idea of the invention, using exemplary embodiments with reference to the drawings, whereby we expressly refer to the drawings with regard to all details according to the invention that are not explained in greater detail in the text. The figures shown in.

DETAILED DESCRIPTION

Figure 1:
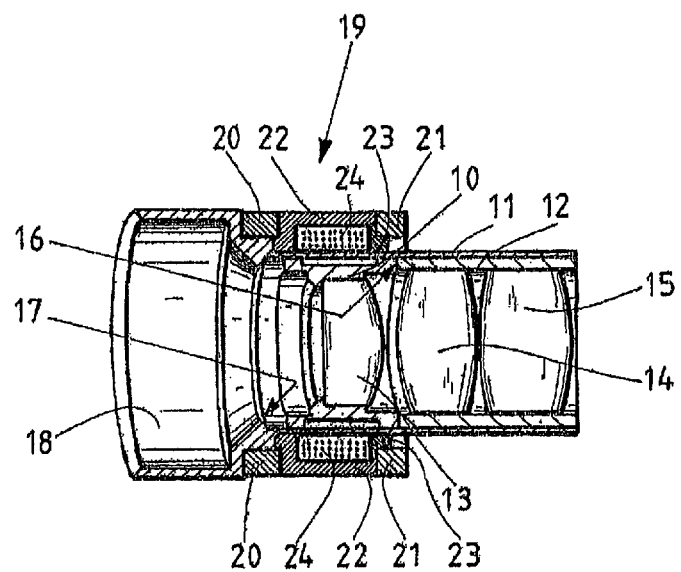
FIG. 1 illustrates a schematic sectional representation through a part of an endoscope with an actuator.

In the drawings, the same or similar types of elements and/or parts are provided with the same reference numbers so that a re-introduction is omitted.

FIG. 1 shows a schematic sectional representation through a part of an endoscope with an actuator. The actuator can be arranged in a shaft (not shown) of an endoscope. In FIG. 1, the shaft of the endoscope would be arranged around the actuator, namely with a diameter which is slightly larger than the outer diameter of the distal end 18 of the sliding tube 11.

The sliding tube 11, which can be made of a metal or plastic, wherein it is important here that it is made of non-magnetic materials, serves as a guide for the axially displaceable rotor 10. The rotor 10, designed as a displaceable element, can have for example a lens 13, which is part of an objective, which also has lenses 14 and 15, which are inserted into a locked holding element 12 and are correspondingly held.

The locked holding element 12 is locked or respectively attached in the sliding tube 11 and defines a stop 16. An additional stop 17 to the distal end is also defined by the sliding tube 11 through a collar inwards. In this exemplary embodiment according to FIG. 1, it is a rotationally symmetrical structure, in which an axially displaceable rotor 10 is provided. The axially displaceable rotor 10 can be displaced from a proximal position in FIG. 1 to the left towards the stop 17 into a distal position. The displaceable element 10 is designed as a type of sleeve, which is made in particular of a magnetically soft material, such as a ferromagnetic material or respectively has this material.

Besides being made of ferromagnetic and/or paramagnetic material, the displaceable rotor 10 can also have a friction-reducing coating on the surface, which is arranged towards the inside wall of the sliding tube 11.

The rotor 10 that is axially displaceable in the sliding tube 11 has a distal pole shoe and a proximal pole shoe, which interact with the magnetic field of the permanent magnets 20 and 21, which are designed as rings and are arranged in a rotationally symmetrical manner around the longitudinal axis of the electromagnetic actuator. A first intermediate part 22 and a second intermediate part 23 made of paramagnetic or ferromagnetic material, which are also designed with pole shoes or as pole shoes, are provided between the permanent magnets 20 and 21. The first intermediate part 22 and the second intermediate part 23 can also be one-piece, i.e. form a single intermediate part.

Furthermore, a spool 24 is provided, which is surrounded to the outside by the first intermediate part 22 and the second intermediate part 23 and is surrounded to the inside except for the interruption by the sliding tube 11 also by paramagnetic and/or ferromagnetic material of the displaceable rotor 10. A very strong strengthening of the electromagnetic field is hereby achieved. The stator 19 of the electromagnetic actuator consists mainly of the two permanent magnetic rings 20 and 21, the two intermediate parts 22 and 23 and of the spool 24.

Figure 2:
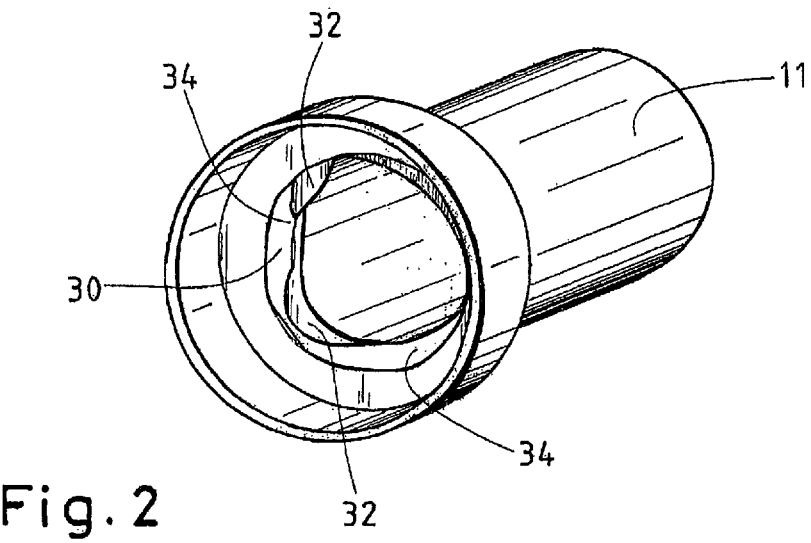
FIG. 2 illustrates schematically a section of a sliding tube of an electromagnetic actuator.

FIG. 2 shows schematically in a perspective view an end-side section of the sliding tube 11, wherein the sliding tube 11 has a receiving cavity 30 on the end shown. The receiving cavity 30 has a non-round shaped inner contour as rotary gate, wherein the receiving cavity 30 interacts with the contour of a rotor positioning key. The receiving cavity 30 has for this on its circumference recesses 32 and undercuts 34 for the rotary gate, which are arranged at regular intervals in the circumferential direction of the sliding tube 11.

The undercuts 34 thereby form rear stops or respectively outside stops for the rotor positioning key after insertion of a rotor positioning key into the receiving cavity 30. The recesses 32 and undercuts 34 arranged alternating in the circumferential direction are arranged evenly in the circumferential direction. In one embodiment, the recesses 32 and the undercuts 34 can hereby be arranged irregularly in the circumferential direction.

Figure 3:
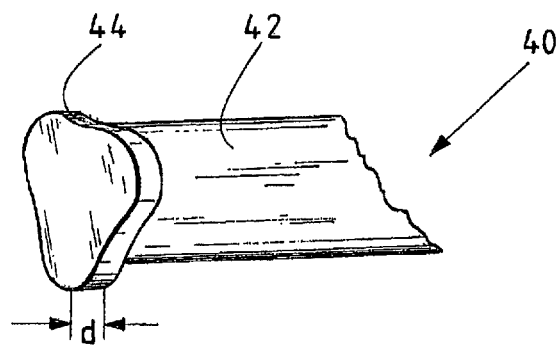
FIG. 3 illustrates schematically a perspective representation of a rotor positioning key according to the invention in a perspective view.

FIG. 3 shows schematically in detail a perspective representation of a rotor positioning key 40 for the rotary gate of the receiving cavity. The rotor positioning key 40 has thereby a rotatable shaft 42, on the end of which is arranged a widened key head 44. The key head 44 is thereby designed in a star-shaped or a star-like manner. The key head 44 that is insertable into the receiving cavity has a thickness d, which corresponds to the stroke length of the rotor in the sliding tube 11 after adjustment of a rotor in the sliding tube 11. The rotor positioning key 40 is hereby inserted into the receiving cavity 30 during the adjustment of the rotor arranged inside the sliding tube 11, wherein the rotor positioning key 40 is twisted after arrangement of the rotor positioning key 40 in the receiving cavity 30. The rotor positioning key 40 is thus releasably locked inside the sliding tube 11 for adjusting the stroke length of the rotor.

The key head 44 has a non-round outer contour, wherein the outer contour of the key head 44 is designed in a star-like manner, wherein the shape of the key head 44 is designed in a shape-complementary manner to the arrangement of the recess 32 and the undercuts 34 of the receiving cavity 30 as well as the rotary gate of the receiving cavity. The rotor positioning key 40 is hereby inserted in an accurately fitting manner into the receiving cavity 30 during insertion of the key head 44 and is subsequently locked by twisting of the rotor positioning key so that the protrusions or respectively tongue-like projections of the key head 44 are arranged in the area of the undercuts 32.

In the case of this positioning of the rotor positioning key 40, the rotor and a stopper arranged in the sliding tube 11 are subsequently pressed with force against the outer contact surface of the key head 44 facing the rotor so that the stopper is subsequently connected with the sliding tube, for example through adhesion. The rotor positioning key 40 is then rotated back and removed from the receiving cavity 30. Space for the stroke of the rotor inside the sliding tube 11 is hereby created between the rotor and the open or respectively opened end of the sliding tube 11.

Figure 4:
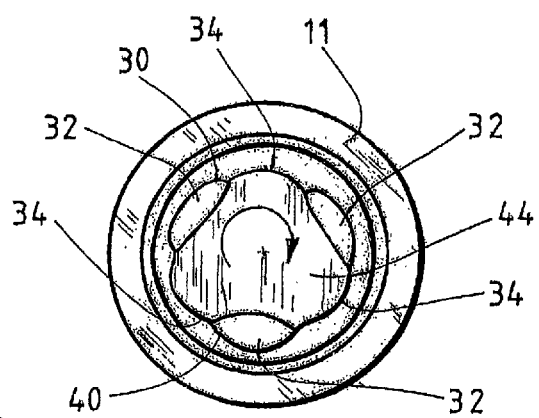
FIG. 4 illustrates a top view of an N side of the sliding tube with rotor positioning key arranged in it.

FIG. 4 shows schematically in a side view the arrangement of the key head 44 in the receiving cavity 30 in the twisted state or respectively locked state of the rotor positioning key 40. The tongue-like protrusions of the key head 44 are hereby arranged behind the undercuts 34 of the receiving cavity 30.

In the exemplary embodiment shown in FIG. 4, the receiving cavity 30 has three abutment points or support points for the rotor positioning key 40. A stop level or respectively abutment level for the key head 44 is hereby provided using the three support points. Within the framework of the invention, it is also conceivable that more than three support points are provided for the key head 44 through the receiving cavity.

All named characteristics, including those taken from the drawings alone and also individual characteristics, which are disclosed in combination with other characteristics, are considered alone and in combination as essential for the invention. Embodiments according to the invention can be realized by individual characteristics, or a combination of several characteristics.

LIST OF REFERENCE NUMBERS

10 Rotor
11 Sliding tube
12 Fixed holding element
13 Lens
14 Lens
15 Lens
16 Stop
17 Stop
18 Distal end
19 Stator
20 Permanent magnet
21 Permanent magnet
22 1st intermediate part
23 2nd intermediate part
24 Spool
30 Receiving cavity
32 Recess
34 Undercut
40 Rotor positioning key
42 Shaft
44 Key head
d Thickness of key head

What is claimed is:

1. An actuator for a surgical instrument, the actuator comprising:
   a sliding tube;
   a stator; and
   an axially displaceable rotor arranged in said sliding tube;
   wherein the sliding tube has at one end a receiving cavity for a rotor positioning key, the receiving cavity being configured such that after the rotor positioning key has been positioned in the receiving cavity, and after the rotor positioning key has been twisted in the receiving cavity, the rotor positioning key is releasably locked, wherein the actuator is a bistable, electromagnetic actuator, wherein the receiving cavity comprises a non-round shaped inner contour as a rotary gate, and wherein a circumference of the receiving cavity comprises recesses and undercuts for the rotary gate, and wherein the rotor positioning key is provided for adjusting the stroke of the rotor in the sliding tube of the actuator.

2. The actuator according to claim 1, wherein the receiving cavity has at least one stop for the rotor positioning key.

3. The actuator according to claim 1, wherein the receiving cavity is adjusted in one or more of a shape-complementary and a functionally complementary manner to the contour of a key head of the rotor positioning key.

4. The actuator according to claim 3, wherein the receiving cavity has a non-round cross-sectional contour.

5. The actuator according to claim 4, wherein the non-round cross-section contour is star-shaped.

6. The actuator according to claim 4, wherein the non-round cross-section contour is a polygon.

7. The actuator according to claim 3, wherein the key head has a thickness that corresponds to the stroke length of the rotor in the sliding tube after adjustment of the rotor in the sliding tube.

8. The actuator according to claim 1, wherein the actuator is for use with a surgical instrument.

9. The actuator according to claim 1, wherein the surgical instrument is an endoscope.

10. The actuator according to claim 1, wherein the sliding tube further comprises a locked holding element in the sliding tube that defines a stop.

11. The actuator according to claim 1, wherein the axially displaceable rotor is formed of a magnetically soft material.

12. The actuator according to claim 1, wherein the axially displaceable rotor further comprises a friction-reducing coating on a surface of the axially displaceable rotor.

13. A rotor positioning key for a rotor of a surgical instrument, wherein the rotor positioning key is releasably lockable in a sliding tube of the actuator according to claim 1, wherein the rotor positioning key has an end-side, widened key head for arrangement and for insertion into the receiving cavity of the sliding tube and a key shaft for twisting the rotor positioning key, wherein the key head is configured in a non-round manner, and wherein the key head has a thickness that corresponds to the stroke length of a rotor in the sliding tube after adjustment of the rotor in the sliding tube, and wherein the rotor positioning key is provided for adjusting the stroke of the rotor in the sliding tube of the actuator.

14. The rotor positioning key according to claim 13, wherein the non-round cross-section contour is star-shaped.

15. The rotor positioning key according to claim 13, wherein the non-round cross-section contour is a polygon.

* * * * *